United States Patent
Bornhop et al.

(10) Patent No.: US 7,130,060 B2
(45) Date of Patent: Oct. 31, 2006

(54) REFRACTIVE INDEX DETERMINATION BY MICRO INTERFEROMETRIC REFLECTION DETECTION

(75) Inventors: Darryl J. Bornhop, Nashville, TN (US); Peter Eskil Andersen, Roskilde (DK); Henrik Schiott Sorensen, Roskilde (DK); Henrik Pranov, Lyngby (DK)

(73) Assignees: Texas Tech University System, Lubbock, TX (US); Technical University of Denmark, Lyngby (DK); Riso National Laboratory, Roskilde (DK)

( * ) Notice: Subject to any disclaimer, the term of this patent is extended or adjusted under 35 U.S.C. 154(b) by 0 days.

(21) Appl. No.: 11/070,273

(22) Filed: Mar. 3, 2005

(65) Prior Publication Data

US 2006/0012800 A1 Jan. 19, 2006

Related U.S. Application Data

(63) Continuation of application No. PCT/US03/25849, filed on Sep. 4, 2003.

(30) Foreign Application Priority Data

Sep. 5, 2002 (GB) ................................ 0220684.5

(51) Int. Cl.
*G01B 9/02* (2006.01)
(52) U.S. Cl. .................................. 356/517
(58) Field of Classification Search ................ 356/517, 356/503, 504
See application file for complete search history.

(56) References Cited

U.S. PATENT DOCUMENTS

| | | | | |
|---|---|---|---|---|
| 4,067,651 A | * | 1/1978 | Watkins | 356/503 |
| 5,325,170 A | * | 6/1994 | Bornhop | 356/517 |
| 6,130,439 A | * | 10/2000 | Le Menn | 356/517 |
| 6,130,748 A | * | 10/2000 | Kruger et al. | 356/450 |
| 6,381,025 B1 | * | 4/2002 | Bornhop et al. | 356/517 |
| 6,386,050 B1 | * | 5/2002 | Yin et al. | 73/861.95 |
| 6,643,018 B1 | * | 11/2003 | Chavanne | 356/338 |
| 6,809,828 B1 | * | 10/2004 | Bornhop et al. | 356/517 |
| 6,940,604 B1 | * | 9/2005 | Jung et al. | 356/503 |
| 2003/0090669 A1 | * | 5/2003 | Jung et al. | 356/450 |
| 2006/0012800 A1 | * | 1/2006 | Bornhop et al. | 356/517 |

OTHER PUBLICATIONS

Valcarcel, M. et al, "We Need Reliable Ways To Bypass Preliminary Operations In (Bio)Chemical Measurement," Trends in Analytical Chemistry, vol. 21 ( No. 4), 2002, p. 211-212.

Hanrahan, G. et al, "High Temporal And Spatial Resolution Environmental Monitoring Using Flow Injection With Spectroscopic Detection," Trends in Analytical Chemistry, vol. 21 ( No. 4), 2002, p. 233-239.

(Continued)

*Primary Examiner*—Gregory J. Toatley, Jr.
*Assistant Examiner*—Patrick Connolly
(74) *Attorney, Agent, or Firm*—Jones, Tullar&Cooper, P.C.

(57) ABSTRACT

A method and an apparatus for absolute refractive index measurements are disclosed, wherein a beam of spatially coherent laser light is directed perpendicularly on to a side of a capillary tube (12) and back reflected light is detected (16) over a range of angles (22) with respect to the incident light beam. The refractive index of a liquid contained in the capillary is determined from the angle at which a marked change in the intensity of the interference fringes of the interference pattern formed by said back reflected light is observed or from the amplitude of a low frequency component of the angular variation of the intensity of interference fringes.

24 Claims, 12 Drawing Sheets

OTHER PUBLICATIONS

Schult, K. et al, "Disposable Optical Sensor Chip For Medical Diagnostis: New Ways In Bioanalysis," Anal. Chem., vol. 71, 1999, p. 5430-5435.

Valcarcel, M. et al, "Continuous Flow Systems for Rapid Sample Screening," Trends In Analytical Chemistry, vol. 21, 2002, p. 251-258.

Zolotov, Y.A. et al, "Test Methods For Extra-Laboratory Analysis," Trends In Analytical Chemistry, vol. 21 ( No. 4) 2002, p. 302-319.

Patel, P.D., "(Bio)sensors For Measurement Of Analytes Implicated In Food Safety: A Review," Trends in Analytical Chemistry, vol. 21 ( No. 2), 2002, p. 96-115.

Wang, J., "Portable Electrochemical Systems," Trends in Analytical Chemistry, vol. 21 ( No. 4), 2002, p. 226-232.

Francis, P.S. et al, "Analytical Methodology For The Determination Of Urea: Current Practice And Future Trends," Trends in Analytical Chemistry, vol. 21 ( No. 5), 2002, pp. 389-400.

Zhou, F. et al, "High-Throughput Fast-Scan Anodic Stripping Voltammetry In A Microflow System," Anal. Chem., vol. 69, 1997, p. 728-733.

Rigby, G.P. et al, "In Vivo Glucose Monitoring With Open Microflow-Influences of Fluid Composition And Preliminary Evaluation In Man," Analytica Chimica Acta, vol. 385, 1999, p. 23-32.

Aiello, M. et al, "A Sensitive Small-Volume UV/Vis Flow Cell And Total Absorbance Detection System For Micro-HPLC," Anal. Chem. , vol. 73, 2001, p. 1387-1392.

Olescuk, R.D. et al., "Analytical Microdevices For Mass Spectrometry," Trends in Analytical Chemistry, vol. 19 ( No. 6), 2000, p. 379-388.

Lagerwerf, F.M. et al, "Exploring The Boundaries Of Bioanalytical Quantitative LC-MS-MS," Trends in Analytical Chemistry, vol. 19 ( No. 7), 2000, p. 418-427.

Lurie, I.S. et al, "Profiling Of Impurities In Heroin By Capillary Electrochromatography And Laser-Induced Fluorescence Detection," Journal of Chromatography A, vol. 924, 2001, p. 421-427.

Senior, K., "Fingerprinting Disease With Protein Chip Arrays," Molecular Medicine Today, vol. 5, Aug. 1999, p. 326-327.

Hack, N.J. et al, "Green Fluorescent Protein as a Quantitative Tool," Journal of Neuroscience Methods, vol. 95, 2000, p. 177-184.

Xia, Y. et al, "Softlithographie," Angew.Chem., vol. 110, 1998, p. 568-594.

Kutter, J.P. , "Current Developments in Electrophoretic and Chromatographic Separation Methods On Microfabricated Devices," Trends in Analytical Chemistry, vol. 19 ( No. 6), 2000, p. 352-363.

McDonald, J.C. et al, "Fabrication of Microfluidic Systems in Poly(dimethylsiloxane)," Electrophoresis, vol. 21, 2000, p. 27-40.

Terry, S.C. et al, "A Gas Chromatographic Air Analyzer Fabricated On a Silicon Wafer," IEEE Transactions of Electron Devices, vol. 26 ( No. 12), Dec. 1979, p. 1880-1886.

Heideman, R.G. et al, "Remote Opto-Chem. Sensing With Extreme Sensitivity: Des. Fabrication and Perf. of a Pigtailed Integ. Opt. Phase-Modulated Mach-Zehnder Interferometer Syst.," Sensors & Act.B, vol. 61, 1999, p. 100-127.

Borhop, D.J. , "Microvolume Index of Refraction Determinations by Interferometric Backscatter," Applied Optics, vol. 34 ( No. 18), Jun. 20, 1995, p. 3234-3239.

Swinney, K. et al, "Ultrasmall Volume Refractive Index Detection Using Microinterferometry," Review of Scientific Instruments, vol. 71 ( No. 7), Jul. 2000, p. 2684-2692.

Swinney, K. et al, "Micro-Interferometric Backscatter Detection Using A Diode Laser," Analytica Chimica Acta , vol. 400, 1999, p. 265-280.

Markov, D. et al, "Nanoliter-Scale Non-Invasive Flow-Rate Quantification Using Micro-Interferometric Back-Scatter And Phase Detection," Fresenius Journal of Anal. Chem., vol. 371, 2001, p. 234-237.

Swinney, K. et al, "Noninvasive Picoliter Volume Termometry Based On Backscatter Interferometry," Electrophoresis, 2001, p. 2032-2036.

Kerker, M. et al, "Scattering of Electromagnetic Waves From Concentric Infinite Cylinders," Journal of the Optical Society of America, vol. 51 ( No. 3), May 1961, p. 506-508.

Watkins, L.S., "Scattering From Side-Illuminated Clad Glass Fibers For Determination of Fiber Parameters," Journal of the Optical Society of America, vol. 64 ( No. 6), Jun. 1974, p. 767-772.

Marcuse, D. et al, "Light Scattering From Optical Fibers With Arbitrary Refractive-Index Distributions," Journal of the Optical Society of America, vol. 65 ( No. 4), Apr. 1975, p. 367-375.

Horton, R. et al, "Interference Patterns Of A Plane-Polarized Wave From A Hollow Glass Fiber," Journal of the Optical Society of America, vol. 63 ( No. 10), Oct. 1973, p. 1204-1210.

Tarigan, H.J. et al, "Capillary-Scale Refractive Index Detection By Interferometric Backscatter," Anal. Chem., vol. 68, 1996, p. 1762-1770.

Markov, D. et al, "Nanoliter-Scale Non-Invasive Flow-Rate Quantification Using Micro-Interferometric Back-Scatter And Phase Detection," Fresenius' Journal of Anal. Chem., vol. 371, 2001, p. 234-237.

* cited by examiner

REFRACTIVE INDEX DETERMINATION BY MICRO INTERFEROMETRIC REFLECTION DETECTION

CROSS REFERENCE TO RELATED APPLICATIONS

This application is a Continuation, under 35 U.S.C. 120 and 365(c), of copending International Application No. PCT/US2003/025849, which was filed on Sep. 4, 2003 and designates the United States.

BACKGROUND OF THE INVENTION

1. Field of the Invention

The present invention relates to methods and apparatus for the determination of refractive index, including the determination of the absolute value of the refractive index of a sample.

2. Description of the Background Art

Rapid monitoring and detection of ultra small volume samples is in great demand[1]. Two major areas are environmental monitoring[2] and point of care detection[3,4]. This covers a huge range from drinking water quality[5] and food quality[6] to determination of glucose[7] and urea[8]. Several detection techniques have the capability to perform fast measurements on small amounts of analyte. Well-established techniques include electrochemistry[9,10] mass spectrometry[11,12,13] and optical detection[14,15]. Not all are equally fast since sample preparation often is extensive and requires time-consuming steps such as chemical tagging of molecules[16]. More or less complex structures are fabricated to guide the samples to the detector[17,18]. This is done to scale down the required amount of analyte as well as size and cost of the entire system into miniaturized total analysis systems[19,20]. Simple optical systems are available to perform sensitive measurements on small volumes[21]. One analytical approach, micro interferometric backscatter detection (MIBD), derives from the observation that coherent light impinging on a cylindrically shaped capillary produces a highly modulated interference pattern. Typically, MIBD analyses reflections from a capillary tube filled with a liquid of which one wants to measure the refractive index. The technique was first used and described by Bornhop et al.[22,23]. In their work[24] the technique has previously been shown capable of measuring changes in refractive index of liquids on the order of $10^{-7}$. The MIBD technique is a simple and universal method of detecting refractive index changes in small volumes of liquid. It has been applied to monitor changes in concentrations of solutes[25], flow rates[26] and temperature[27], all conducted in nanoliter volumes. The MIBD scheme and systems of similar geometrical configurations (to that of the MIBD scheme) have previously been modeled by wave theory[28,29,30] or optical ray tracing[31].

The MIBD technique is based on interference of laser light after it is reflected from different regions in a capillary or like sample container. Suitable methods and apparatus are described in U.S. Pat. No. 5,325,170 and WO-A-01/14858. The reflected or back scattered light is viewed across a range of angles with respect to the laser light path. The reflections generate an interference pattern that moves in relation to such angles upon changing refractive index of the sample. The small angle interference pattern traditionally considered has a repetition frequency in the refractive index space that limits the ability to measure refractive index to refractive index changes causing one such repetition. Such refractive index changes are typically on the order of three decades.

SUMMARY OF THE INVENTION

Our modeling of the MIBD technique has now shown that other intensity variations in the pattern are present for larger reflection angles, as we have also confirmed experimentally. By considering these variations we have established methods by which it is possible to extend the dynamic measurement range and to make an absolute refractive index measurement. One method described below utilizes variations in the Fresnel coefficients while a second preferred approach is based on the refractive index dependent onset of total internal reflection angles. With the second approach we have been able to measure the absolute refractive index of a liquid with a precision of $2.5 \times 10^{-4}$.

Accordingly, the present invention now provides a method for performing a measurement of refractive index comprising directing a coherent light beam along a light path to impinge on a first light transmissive material and pass there through, to pass through a sample which is to be the subject of the measurement, and to impinge on a further light transmissive material, the sample being located between the first and further materials, detecting reflected light over a range of angles with respect to the light path, the reflected light including reflections from interfaces between different substances including interfaces between the first material and the sample and between the sample and the further material which interfere to produce an interference pattern comprising alternating lighter and darker fringes spatially separated according to their angular position with respect to the light path, and conducting an analysis of the interference pattern to determine there from the refractive index, wherein the analysis comprises observation of a parameter of the interference pattern which is quantitatively related to sample refractive index dependent variations in the intensity of reflections of light which has passed through the sample.

In accordance with preferred variants of this procedure, said analysis comprises one or both of:

(a) the observation of the angle with respect to the light path at which there is an abrupt change in the intensity of the lighter fringes, or (b) the observation of the amplitude of a low frequency component of the variation of intensity between the lighter and darker fringes.

The first of these (a), relies upon the dependency of the angle at which total internal reflection occurs at an interface between the sample and the said further material on the refractive index of the sample. The second (b), relies upon the dependency of the intensity of reflections from that interface on the said refractive index as given by the Fresnel coefficients.

The first material and the further material are usually composed of the same substance and may be opposite side walls of a container within which the sample is held or conducted. For instance, the sample may be contained in, e.g. flowed through, a capillary dimensioned flow channel such as a capillary tube. The side wall of the capillary tube nearer the light source is then the "first material" and the opposite side wall is the "further material". The cross-sectional depth of the channel is limited only by the coherence length of the light and its breadth is limited only by the width of the light beam. Preferably, the depth of the channel is from 1 to 10 um, but it may be from 1 to 20 um or up to 50 um or more, e.g up to 1 mm or more. However, sizes of up to 5 mm or 10 mm or more are possible. Suitably, the breadth of the channel is from 0.5 to 2 times its depth, e.g. equal to its depth.

The sample may also be contained in a flow channel of appropriate dimensions in substrate such as a microfluidic chip. The method may therefore be employed to obtain a read out of the result of a reaction conducted on a "lab on a chip" type of device.

Preferably, at least one said interface involving said sample at which light is reflected is curved in a plane containing said light path, said curved interface being convex in the direction facing the incoming light if it is the interface between the first material and the sample and being concave in the direction facing the incoming light if it is the interface between the sample and the further material. Preferably, the sample is in a channel of circular or generally semi-circular cross-section.

The sample will normally be a liquid, and may be flowing or stationary. However, in principle, the sample can be a solid or a gas. The first and/or further materials will normally be solid but in principle can be liquid, e.g. can be formed by a sheathing flow of guidance liquid (s) in a microfluidic device, with the sample being sheathed flow of liquid between such guidance flows.

In contrast to earlier described methods, the invention preferably makes use of observations of the interference pattern at large angles with respect to the light path, e.g. said range of angles may include angles up to at least 20 degrees or more preferably at least 40 degrees.

The invention includes apparatus for use in performing a method as described, which apparatus comprises a source of spatially coherent light, a sample holder for receiving a sample upon which to perform said method positioned in a light path from said light source, a detector for detecting light reflected from said sample over a range of angles with respect to the light path, and data processing means for receiving measurements of light intensity from said detector and for conducting an analysis thereon, wherein the analysis comprised determining a parameter of an interference pattern produced by said reflected light which parameter is quantitatively related to sample refractive index dependent variations in the intensity of reflections of light which has passed through the sample.

Said data processing means may be adapted to perform an analysis which comprises one or both of:

(a) the determination of the angle with respect to the light path at which there is an abrupt change in the intensity of the lighter fringes, or (b) the determination of the amplitude of a low frequency component of the variation of intensity between the lighter and darker fringes.

The apparatus may comprise means for controlling the temperature of the sample, e.g. a heater and/or a Peltier cooler and a temperature measuring device. In the earlier publications relating to MIBD, the term "back-scatter" is generally used to describe the origin of the light rays that form the interference pattern. On the basis of the theoretical analysis of the origin of the interference pattern presented herein, we prefer the term "reflection" as being more strictly accurate, but the phenomenon referred to by these terms is in each case the same.

The source of coherent light is preferably a laser, suitably a He Ne laser or a diode laser or VCSEL. The laser light may be coupled to the site of measurement by known waveguiding techniques or may be conventionally directed to the measurement site by free space transmission.

The measured refractive index may be indicative of a number of properties of the sample including the presence or concentration of a solute substance, e.g. a reaction product, pressure, temperature or flow rate (e.g. by determining when a thermal perturbation in a liquid flow reaches a detector).

The detector is suitably a CCD array of suitable resolution.

The invention has numerous uses, including but not limited to RI detection for CE (capillary electrophoresis), CEC (capillary electrochromatography) and FIA, physiometry, cell sorting/detection, ultramicrocalorimetry, flow rate sensing and temperature sensing.

The invention includes apparatus as described above wherein said sample holder is configured to allow a sample to flow there through and wherein said sample holder is connected to receive a separated sample from a sample separation device in which components of a mixed sample are separated, e.g. by capillary electrophoresis, capillary electrochromatography or HPLC. Accordingly, viewed from another perspective, the invention provides chromatography apparatus having a refractive index measuring unit as described herein as a detector.

More generally, the sample holder of the apparatus described above may be a flow through passage so that the contents of the channel may be continuously monitored to observe changes in the content thereof. These changes may include the temporary presence of cells and the out flow from the sample holder may be diverted to a selected one of two or more outlet channels according to the measurements of RI observed in the sample holder, e.g. to achieve sorting of cells in response to such measurements.

The sample holder may contain a stationary analytical reagent (e.g. a coating of an antibody, oligonucleotide or other selective binding agent) and changes in the refractive index caused by the binding of a binding partner to said reagent may be observed.

In view of the small sample size which it is possible to observe, the sample holder may contain a biological cell and metabolic changes therein may be observed as changes in the refractive index of the cell.

BRIEF DESCRIPTION OF THE DRAWINGS

The invention will be further described with reference to the accompanying drawings in which.

DETAILED DESCRIPTION OF THE INVENTION

Figure 1:
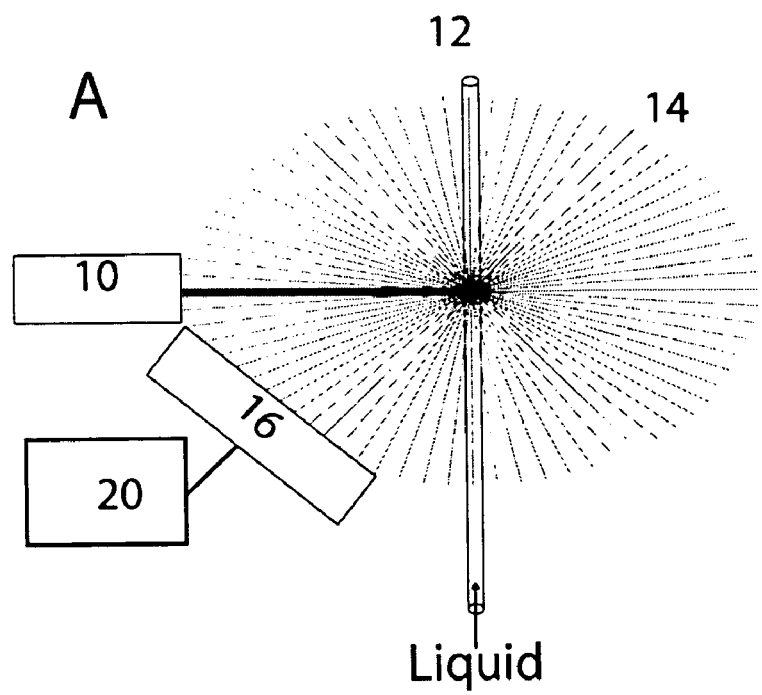
FIG. 1 shows a schematic view of a suitable MIBD experimental setup seen in isometric view (A) and in plan view from the top (B) with a typical interference pattern shown at (C).
Figure 1:
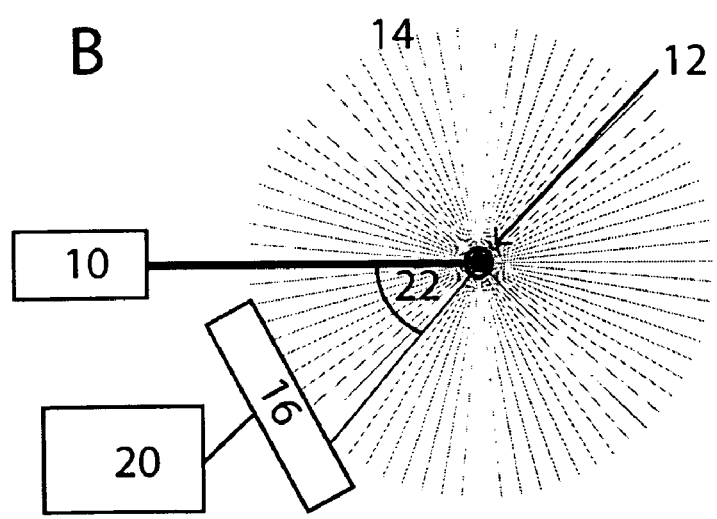
Figure 1:
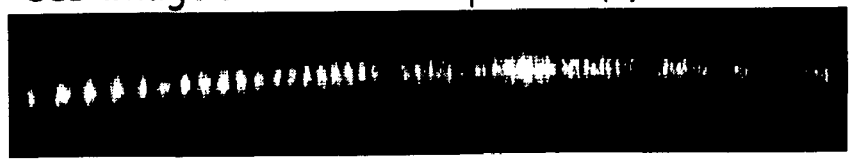

A typical MIBD scheme as previously known is shown in FIG. 1. The system consists of a laser 10 that impinges its beam on a capillary tube 12 filled with a liquid of which one wants to measure refractive index, thereby creating an interference pattern 14. This interference pattern, which changes with changes in the liquid's refractive index, is then measured using a CCD detector 16. A typically observed interference pattern in the reflection direction is seen in C. This is analyzed by data processing means 20.

The demonstrated sensitivity of $10^{-7}$ is reached by following the displacement of the individual light fringes of the interference pattern within 0–3 angular degrees[24] from the directly back reflected direction, as one changes the refractive index of the liquid. The fringe pattern is periodic in refractive index space with a period of the order of $10^{-3}$. This limits the dynamic measurement range to the order of $10^{-3}$, which for many purposes requires additional knowledge about the absolute value of the refractive index.

As the measurement monitors a displacement of the fringe pattern, it is inherently a differential measurement. This requires both calibration for the absolute level of the refractive index as well as for the differential factor. This factor describes the fringe movement corresponding to a given change in the refractive index.

Here, we show how the dynamic range of the MIBD system may be increased. This is done by taking into account other variations of the interference pattern with changing refractive index than those previously considered. The dynamic range is increased without compromising the high differential sensitivity previously reported[24]. The theoretical description of the MIBD scheme has been improved to include an extended optical ray tracing model that matches the range in angular and refractive index space of the experiments, thus providing new information about the structure of the reflected light interference pattern. In contrast to the previously proposed model[32], this model is capable of explaining all frequency components that appear in the interference pattern. Furthermore, the model has been used to predict an abrupt change in the intensity of the reflected light interference fringes, which depends uniquely on the absolute value of the refractive index of the probed sample. Moreover, this feature has been experimentally confirmed. The improved understanding of the MIBD system is used to propose two preferred approaches to an absolute measurement of the refractive index of samples, which are preferably liquids in the refractive index range between water (1.33) and glass (1.50). One approach is based on the measurement of the depth of modulation of the interference pattern caused by variations in the Fresnel coefficients. The second approach is based on the measurement of the total internal reflection angle within the capillary or other sample container.

Previously systems of similar geometry to the MIBD scheme have been modeled by obtaining solutions to Maxwell's equations governing light propagation[33] or by optical ray tracing. Kerker and Matijevic[28] made the first complete model based on solutions to Maxwell's equations describing two concentric cylinders. Watkins confirmed these results experimentally[29]. However Watkins considered optical glass fibers with thick claddings and therefore obtained results significantly different to those observed in MIBD, as the interference pattern is described not to be dependent on the refractive index of the core in the back-scatter angle regime. Marcuse and Presby[30] extended this model to also take into account the case of a thin cladding of the fibers. From their results, an abrupt change in the back-scattered light intensity pattern is observed. However, it was not realized that this abrupt change could be utilized to obtain the absolute refractive index with high precision, since they were attempting to determine the outer radius of the glass fiber, and they were not concerned with the core index. We have discovered that the position of the abrupt change depends on the core index, see below. Horton and Williamson[31] made a ray tracing model of an optical fiber obtaining information about the ratio between inner and outer radii of the fiber. The approach they used is a back calculation assuming a planar wave front of the output. The rays considered in their model are not the same as in our model, as they consider fibers with a thick cladding, and make use of multiple reflections inside the cladding. This is due to the fact that they use significantly different refractive indices of the core than those considered in MIBD. The MIBD system has been modeled using a ray-tracing model by H. Tarigan et al.[32]. However, their model is limited by considering only small angle back-scattered light (0–3 degrees).

We have extended the model to include reflection angles up to 90 (side reflections). This is done in the geometric optics regime by using Snell's law, $$n_i \times \sin(\theta_i) = n_j \times \sin(\theta_j), \quad (1)$$

where $n_i$ and $n_j$ are the refractive indices of the media and $\theta_i$ and $\theta_j$ are the angles of light propagation in the respective media. Furthermore the law of reflection, $|\theta_{in}|=|\theta_{out}|$, is used. For angles beyond a few degrees it is not possible to use the assumption ($\sin \theta \approx \theta$) done by Tarigan et al. This implies that a simple analytical equation cannot be obtained. Our model traces six beams, see FIG. 2, through the system and calculates their interference in a detection plane placed in the far field region. For each type of beam a number of rays (typically 1000) are traced. The information carried along with each ray is its position, angle, intensity and phase. At the detection plane the interference is calculated based on the information packages of all rays. The six beams considered in the model interfere by $$I_{ij} = 2\sqrt{I_i \times I_j} \times \cos(\rho_i - \rho_j) \quad (2)$$

where I is the intensity and ρ is the phase of each individual ray, and i and j are indices for each ray, respectively. The model is developed to also take into account the polymer coating on the capillary, thus requiring six beams. The model assumes circular geometry of the capillary and that the laser can be described by plane waves.

The model assumption of circular geometry of the capillary is justified by the observation that no significant change in the pattern was observed during rotation of the capillary (TSP100170, Polymicro Technologies) along the capillary axis. The tilt of the wave front from the laser (05-LHR-HeNe, Melles Griot) was analyzed using a beam analyzer (CLAS-2D, Wave Front Sciences) and was observed to be less than 0.01 micro radians, thus justifying the assumption of a planar wave front. The smallest spacing of refractive index changes is the thickness of the coating of 12 micrometer.

Therefore the assumption of geometrical optics being adequate is justified since the wavelength used (632.8 nm) is much smaller than the distances otherwise present in the system.

In what follows, modeling and experimental work is based on the use of apparatus as shown in FIG. 1. The MIBD experiments were done by mounting the capillary on a translation stage and making a HeNe laser beam impinge perpendicularly on the capillary. The reflected or backscattered light was collected using a screen and a CCD camera (C4742-95, Hamamatsu). The requirements for the laser are a coherence length of at least twice the diameter of the capillary and a wavelength at which the capillary is transparent. The requirements for the detector are high one-dimensional spatial resolution and an adequate intensity resolution, depending on the application, as will be seen later. Passive temperature control consisting of a large thermal reservoir (an aluminum block) thermally connected to the capillary was used to stabilize temperature. Temperature fluctuations affect the refractive index of the liquid substantially. Active temperature control is only needed if the detection of changes in refractive index of less than $10^{-5}$ is required. In this work passive temperature stabilization is adequate, as the refractive index fluctuations in the system caused by temperature fluctuations in our controlled environment are on the $10^{-5}$ scale, corresponding to $0.1°$ C. temperature fluctuations for water.

Figure 3:
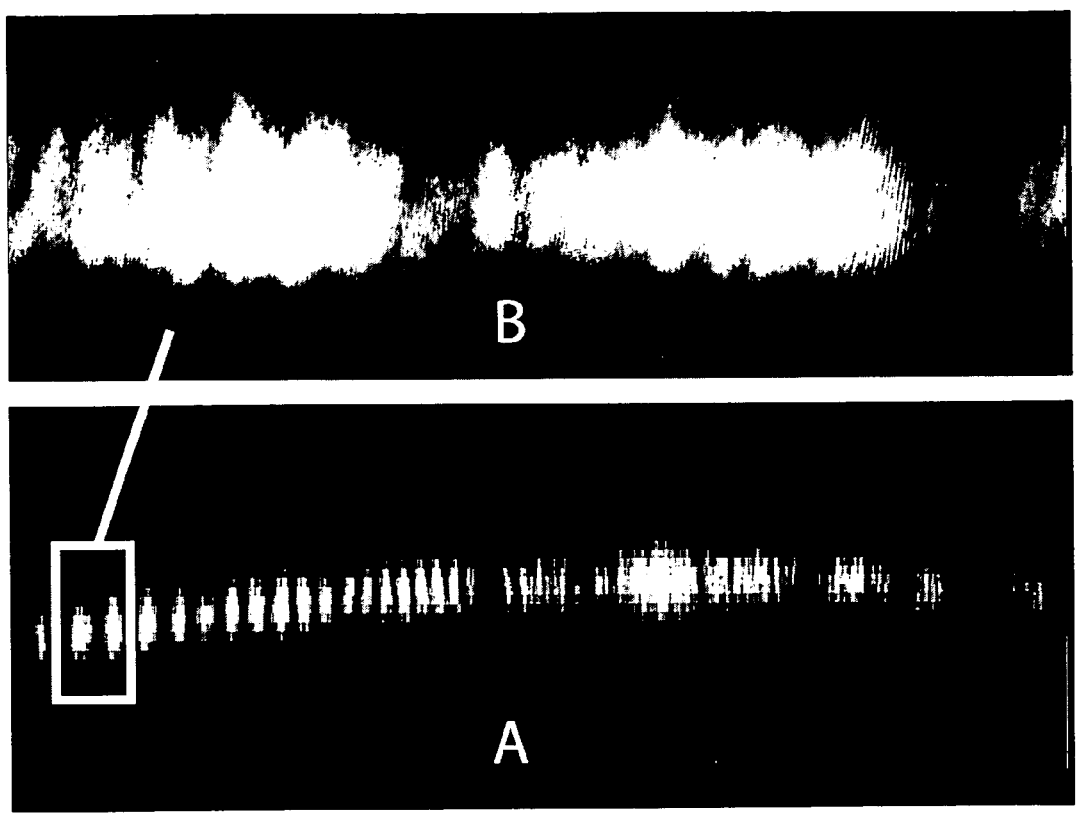
FIG. 3 shows CCD camera images of a typical MIBD interference pattern (A, B).
Figure 4:
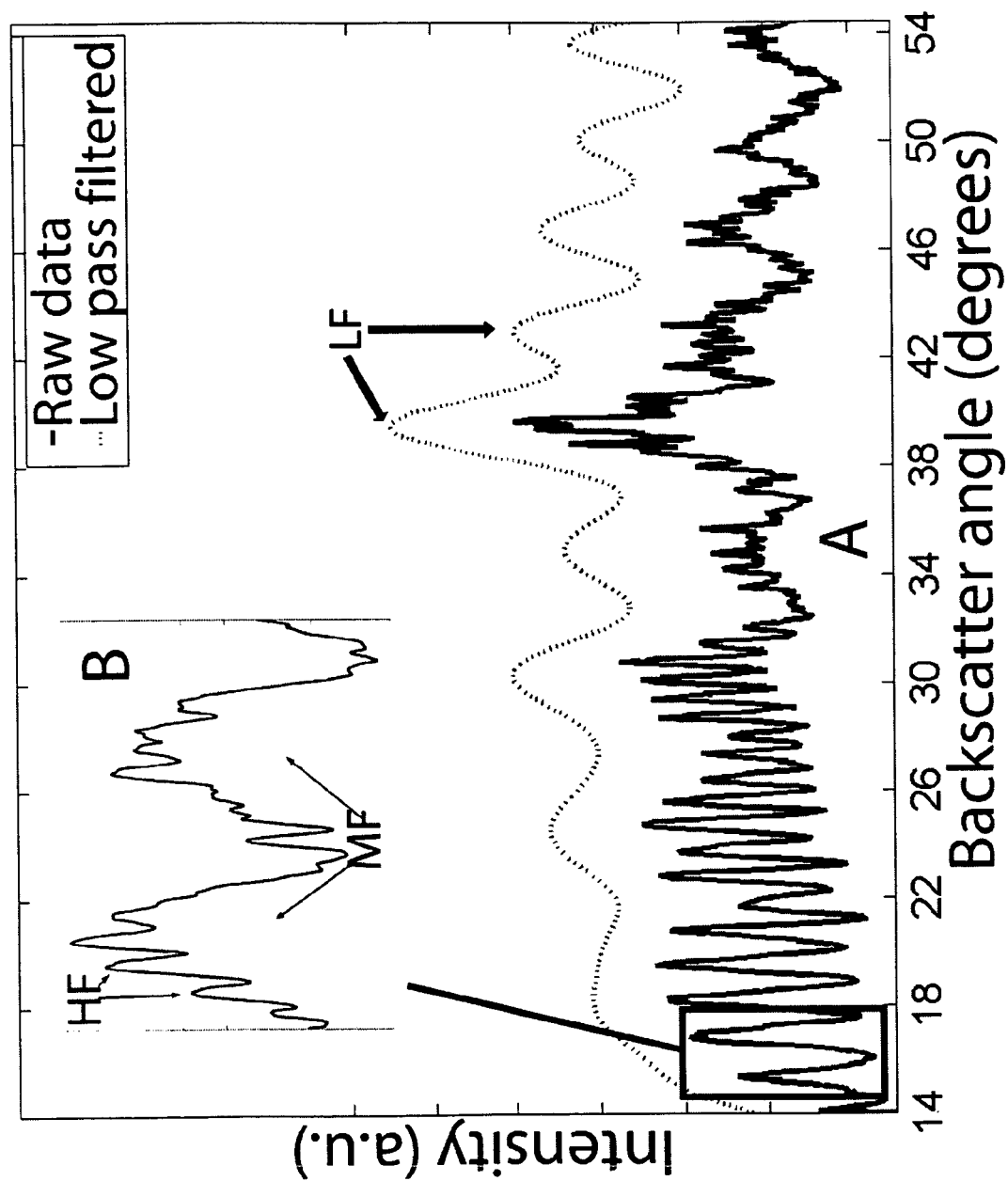
FIG. 4 shows line profiles (A, B) corresponding to interference patterns A, B respectively of FIG. 3.

The capillaries used in the experiments were purchased from Polymicro Technologies (AZ, US). Two sizes of capillaries have been used. The dimensions of the capillaries are 100 μm inner diameter (ID), 165 μm outer diameter (OD) with a 12 μm thick polyimid coating (TSP100170) and 542 μm ID, 673 μm OD with a 24 μm thick polyimid coating (TSP530660), respectively. In the experiments the refractive index was changed from 1.33 to 1.5 by using both sucrose (Sigma Chemicals Company) and NaSCN (Merck) aqueous solutions. The RI of the solutions was measured in a refractometer (RL3, Polskie Zaklady Optyczne, Warsaw) immediately after the sample had been injected into the capillary. A typical interference pattern thus obtained is shown in FIG. 3A, with corresponding line profile of the intensity shown in FIG. 4A. In FIG. 3B two of the fringes in 3A are enlarged, showing a finer structure. A line profile of the intensity from 3B is seen in 4B. The visual appearance is enhanced by low pass filtering, a Fourier filter, of the raw data. The raw data and the low pass filtered data have been offset for clarity. It is seen that the intensity pattern contains multiple frequency components. The period of the fringe pattern corresponding to medium frequency (MF) components is shown in FIG. 4B. Similarly, the period of the fringe pattern corresponding to low frequency (LF) components is shown in FIG. 4A. In the following, we shall refer to these frequency components as frequencies. Under certain circumstances one is able to observe a faster varying component of the intensity profile, here denoted high frequency (HF) variations, see FIGS. 3B and 4B. As one increases the refractive index of the liquid in the capillary the intensity profile shifts towards lower reflection angles, see FIG. 7. However, the high frequency variation component is spatially fixed and does not move as one changes the refractive index in accordance with previous observations[34].

By investigating the experimentally observed frequencies of the fringe pattern, it may be shown by geometrical considerations that the distance between the origin points of the interfering rays (points a through f in FIG. 2) on the capillary are approximately 5 to 10 times larger in the high frequency case than in the medium frequency case. By using geometrical considerations it is possible to calculate the distance between origins of the interfering rays for all frequency components. We found that the distance required to produce the high frequency variations is on the order of the capillary diameter. This indicates that the rays responsible for this high frequency variation are scattered from the edges of the capillary, thereby not being affected by the liquid within the capillary. This hypothesis fits the observed behavior well, since the high frequency component is not observed to be displaced as one changes the refractive index of the liquid in the capillary. Since this component does not move with changing refractive index, and thus cannot be used in a refractive index determination, it will not be considered further in this paper, neither experimentally nor in the modeling of the system.

Figure 2:
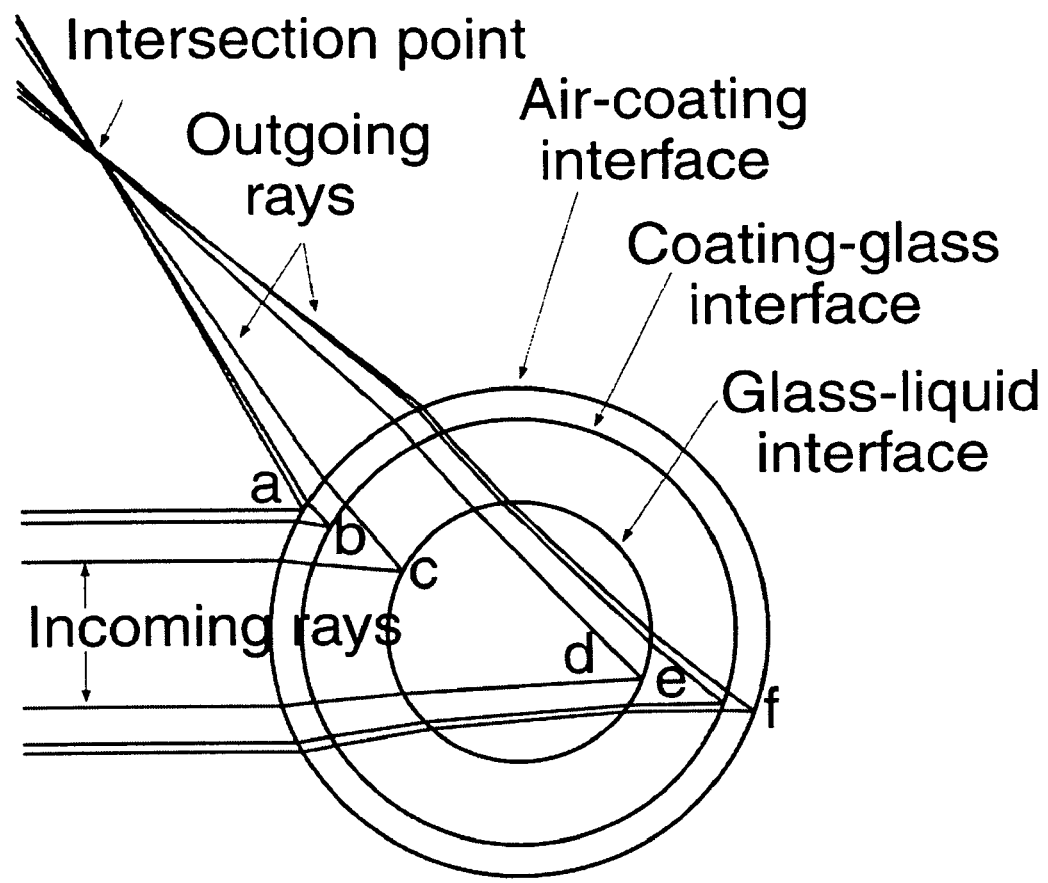
FIG. 2 is a view of the cross-section of the capillary 12 of FIG. 1 showing the ray paths through the capillary system.

The low frequency component is spatially stationary as well, since this component is caused by the common interference between the three rays reflected from the front of the capillary (points a through c in FIG. 2), as well as the common interference between the three rays reflected from the back of the capillary (points d through f in FIG. 2). The displacement of this component is zero for the part originating from the front, since these rays do not traverse the liquid and thus experience the same optical path length by different refractive indices of the liquid. For the second part the displacement is small, because all three rays experience almost the same change in optical path length traversed relative to each other.

In contrast to the high and low frequency components, respectively, the medium frequency component originates from the interference between rays reflected at the front (points a–c in FIG. 2), and at the back of the capillary (points d through f in FIG. 2). These rays experience a large relative change in optical path length traversed, as the rays from the front do not experience a change in optical path length whereas the rays reflected from the back do. It is this relative change in the optical path length between different paths that causes the movement of the medium frequency component of the interference pattern as refractive index changes, yielding the ultra-high sensitivity previously described.

Figure 5:
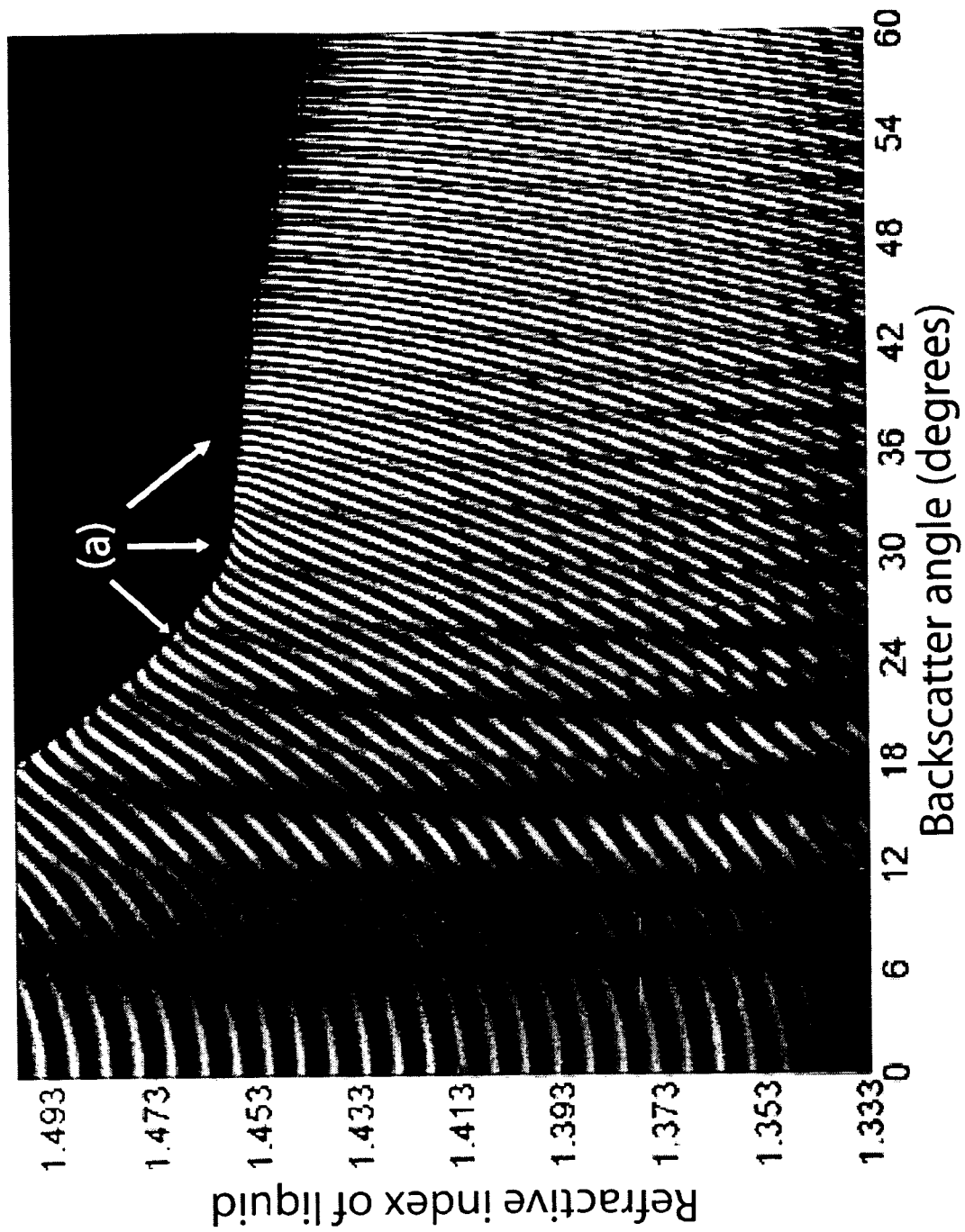
FIG. 5 shows model predictions of the angle dependent variations in the reflected light intensity in the plane perpendicular to the capillary tube of FIG. 1.
Figure 6:
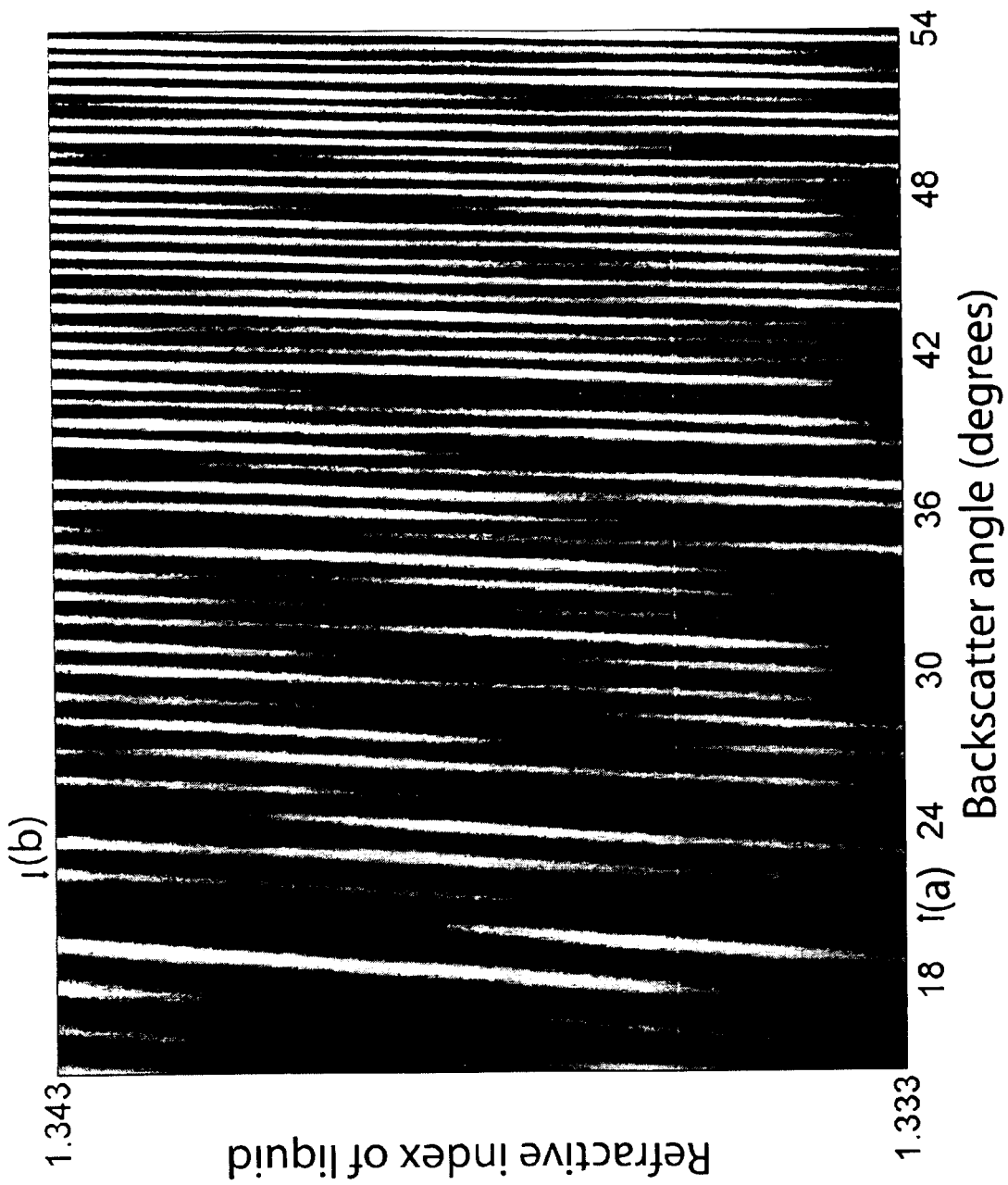
FIG. 6 shows a calculated pattern for a smaller refractive index range from a 100 µm ID/165 µm OD/12 µm coating capillary.

The results from the model are plotted in FIGS. 5 and 6 as function of reflection angle and refractive index of the liquid for a 100 μm ID/165 μm OD/12 um coating capillary. The results have been compiled in this plot by stacking such line plots for closely spaced liquid refractive indices into a two-dimensional overview of the reflection behavior. This plot corresponds to 1643 injections of liquid with different refractive indices. Bands of light (fringes) move towards larger reflection angles as the refractive index is increased. Overlaying vertical band structures of higher and lower light intensity are seen. These structures do not move as the refractive index is changed. An abrupt change in the intensity level (a) is seen moving towards lower back-scattering angles for refractive indices of the liquid above 1.45. The grayscale represents the intensity of the pattern in the given reflection angle for the given refractive index of the liquid in arbitrary units. In FIG. 6 the movement of the fringes at a reflection angle of 20° is measured to be approximately 2.1° per 0.01 refractive index change, measuring from (a) to (b).

Figure 7:
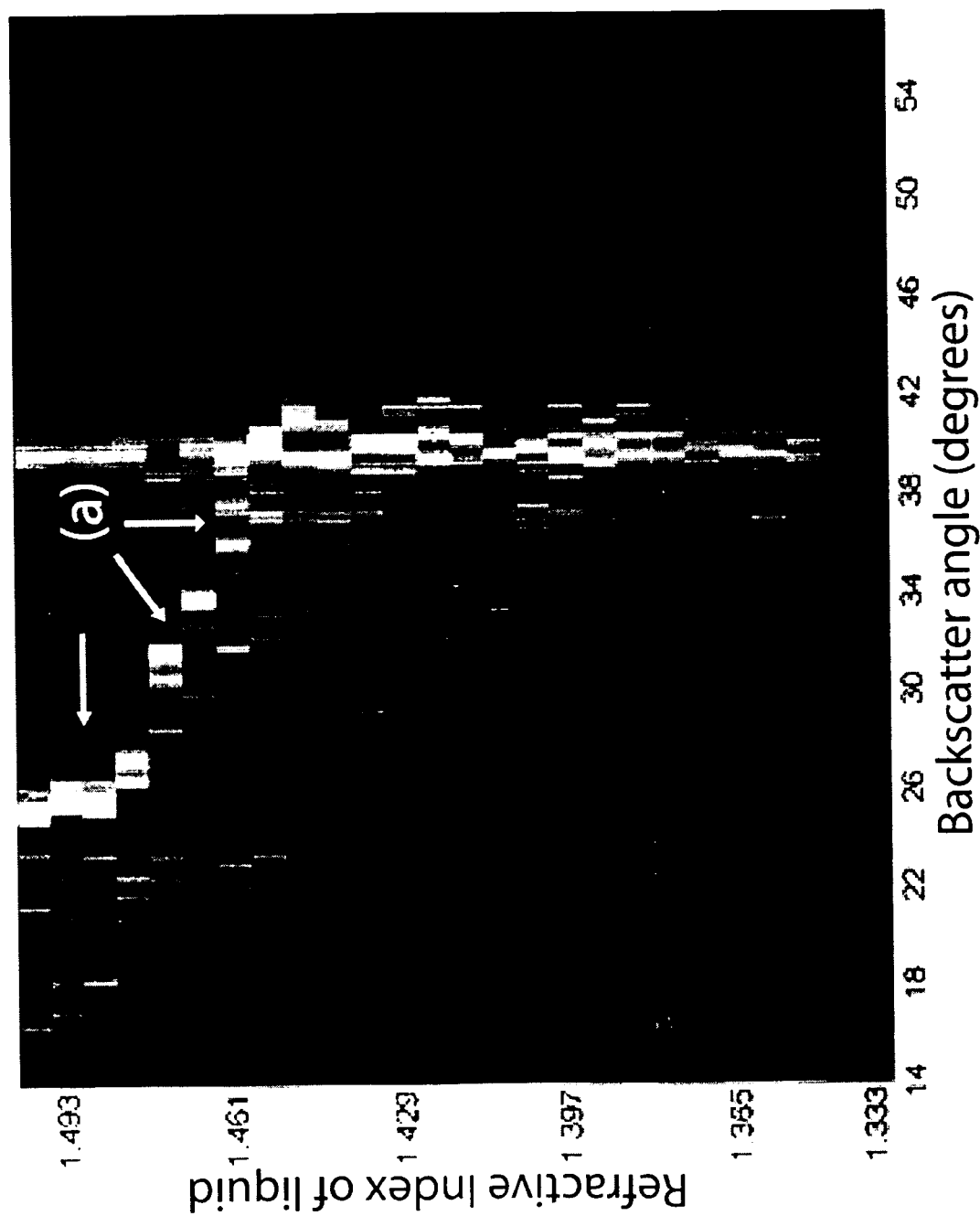
FIG. 7 shows experimentally obtained data from a 100 µm ID/165 µm OD/12 µm coating capillary showing the low frequency variations of the interference pattern as the refractive index is varied.
Figure 8:
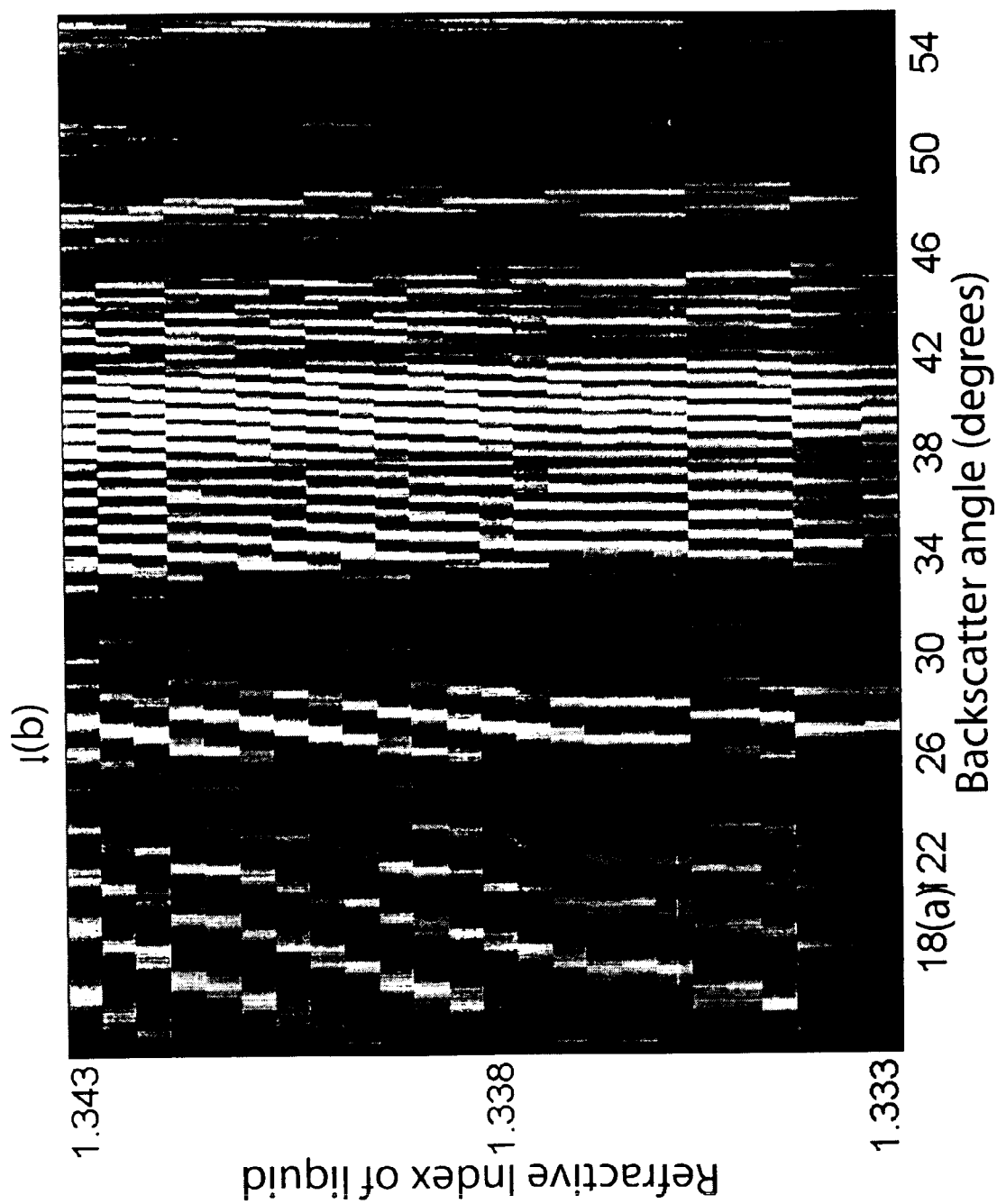
FIG. 8 shows experimentally obtained data for dilute sucrose solutions in a 100 µm ID/165 µm OD/12 µm coating capillary.

Experimentally obtained data are plotted the same way as the model and the results are shown in FIGS. 7 and 8. Here 25 measurements of the interference pattern have been made, each at different refractive index. At each refractive index level a line profile of the interference pattern has been obtained. These measurements have been stacked vertically into one figure. In FIG. 8, the refractive index interval between measurements is less than the change required to move a fringe one fringe-width, thus allowing one to monitor the medium frequency fringes as continuous bands. The movement of these fringes varies with reflection angle. For a reflection angle of 20 this movement is measured to be 4.0 per 0.01 refractive index change, measuring from (a) to (b). Low frequency variations are seen as vertical light bands.

These fringes do not appear to form continuous bands in the vertical refractive index dependent direction due to the large change in refractive index between measurements. An abrupt change in the intensity (a) is seen for high refractive indices (above 1.43), which moves towards lower reflection angles for increasing refractive index.

At each refractive index a line profile of the intensity of the interference pattern has been made (FIGS. 4A and 4B). Each line profile has been extended vertically. The extended line profiles have been stacked into a single plot. These figures are used to directly compare the model and the experiment. In the MIBD experiments two sets of fringes are always present. The fringes moving outwards (medium frequency) with increasing refractive index are measured to move 4.0° when the refractive index is changed by 0.01 at a reflection angle of 20° (a, b in FIG. 8). The model predicts a movement of 2.1° (a, b in FIG. 6). These are the fringes traditionally used for measuring refractive index using the MIBD technique. This model predicts both low frequency and medium frequency variations of the pattern. These frequencies will be discussed below. The low frequency fringes are not moving significantly with changing refractive index. The model predicts no movement of these fringes. The number of these fringes in the model is 13 and in the experiment 10 fringes are observed within a range of reflection angles from 14 to 54°. Both model and experiment shows an abrupt change in intensity at large reflection angles. This abrupt change in intensity is somewhat displaced in the modeled results compared to the experimental results, but it is within experimental error. The movement of this abrupt change in intensity in experiments qualitatively agrees with our modeling of the MIBD system. Although the model does not fit experiment quantitatively, the model does predict the behavior of our MIBD system qualitatively. The predictions of the model have been used to select the proper capillary dimensions for our applications of the MIBD technique.

A first preferred embodiment of the invention performs absolute measurement of refractive index based on Fresnel coefficients. Even though the low frequency variations remain stationary in terms of reflection detection angles, their intensity changes as the refractive index of the liquid changes. As the intensity of the rays are in part determined by the Fresnel coefficients of the surface of reflection, it is possible to configure the system in such a way that the intensity of the low frequency component can be used as a measure for the refractive index on a coarser scale. This may be done by either index matching the coating and the glass tubing, thereby eliminating the reflection from the coating-glass surface (points b and e in FIG. 2) or by stripping the coating off the capillary. The low frequency component is then caused by interference between two rays; the ray reflected by the air-coating (points a and f in FIG. 2) or air-glass interface (points b and e if the coating is removed) and the ray reflected from the glass-liquid interface (points c and d in FIG. 2). Since the intensity of this last ray is determined by the Fresnel coefficients of this surface consisting of glass with constant refractive index and the liquid to be probed, the absolute value of the refractive index of the liquid may be calculated from the relative intensity of the two rays, which is given by the depth of modulation of the low frequency component. This is only possible if the refractive index of the air, glass and coating is known. If one wants to measure depth of modulation to a certain degree, one needs at least this degree of intensity resolution in the detection system. Since our CCD camera has 255 intensity levels we would not be able to acquire more refractive index resolution than the difference in refractive index between air and glass divided by the number of detectable intensity levels, which corresponds to $5 \times 10^{-3}$. A camera with a larger number of intensity levels should therefore be used.

Figure 12:
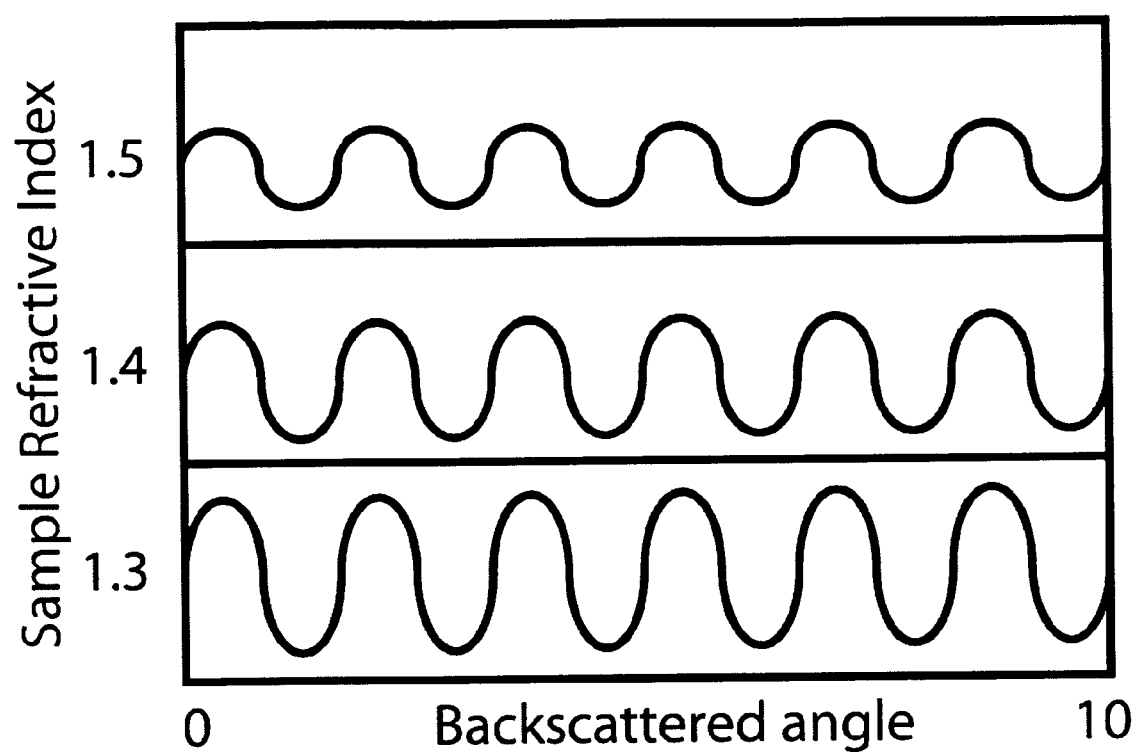
FIG. 12 shows model LF component plots for three different refractive index samples.

However, FIG. 12 shows model LF plots (similar to that marked in FIG. 3) calculated for liquids of three different refractive indices. It can be seen that the amplitude of the modulation is dependent on the refractive index and decreases as the refractive index increases. Suitably one takes the average of the amplitude of the LF peaks over as large an angle range as possible.

A second preferred embodiment relies on the dependence on refractive index of the critical angle at which total internal reflection occurs. The model predicts an abrupt change in intensity moving towards lower reflection angles as the refractive index of the liquid approaches the one of the glass tubing, see line marked by (a) in FIG. 5. This feature of the interference pattern is also observed experimentally, see (a) in FIG. 7, and agrees with the predicted feature in position-refractive index space within experimental error. A feature similar to this has been reported for optical glass fibers[31]. However these fibers have a different optical configuration, and the mechanisms responsible are different. In the case of optical glass fibers the mechanism responsible is grazing of a certain ray on the core of the fiber being dependent of the inner radius of the glass fiber. The mechanism giving rise to the phenomenon in MIBD is total internal reflection in the wall of the capillary, being dependent on the refractive index of the liquid in the capillary. The main source of error is the dimensions of the capillary, which have an uncertainty of 6 μm for the 100 μm ID/165 μm OD/12 um coating capillary according to the manufacturer. The way of determining the absolute value of refractive index on a coarser scale is to look at this feature of the pattern. Both the model and the experiment show an abrupt change in light intensity at higher reflection angles, and the position of this change varies with refractive index. However, using a 100 μm ID/165 pm OD capillary this change takes place at refractive indices 1.40 to 1.50, which is not the measurement range typically of interest for bio analytical applications. Most dilute aqueous solutions of biological relevance have refractive indices in the range from 1.33 to 1.40. By using our model, one is able to calculate the dimensions of the capillary required to make the abrupt intensity change occur in position/refractive index space at refractive indices above 1.33 and at reflection angles inside our measurement range. The mechanism responsible for this abrupt change in intensity is, according to the model, total internal reflection of the rays reflected from the back of the capillary, preventing these rays from being scattered to larger reflection angles, thereby causing a sudden decrease in the intensity of the light at a given limiting angle. This angle varies uniformly with the refractive index and may therefore be used as a measure for the refractive index of the liquid.

Figure 9:
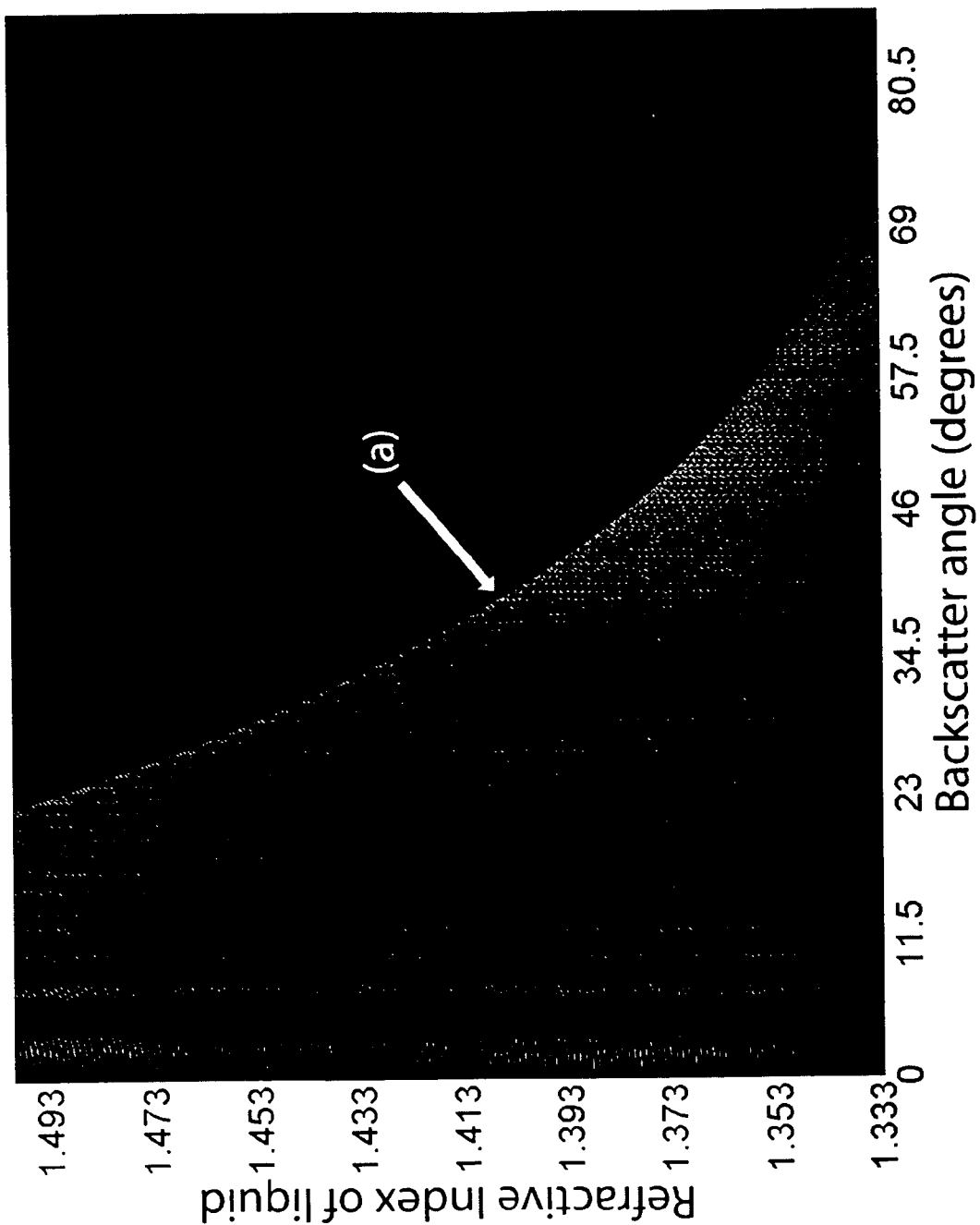
FIG. 9 shows a calculated pattern for a 542 μm ID/673 μm OD/24 μm coating capillary as function of reflection angle and refractive index of the liquid.
Figure 10:
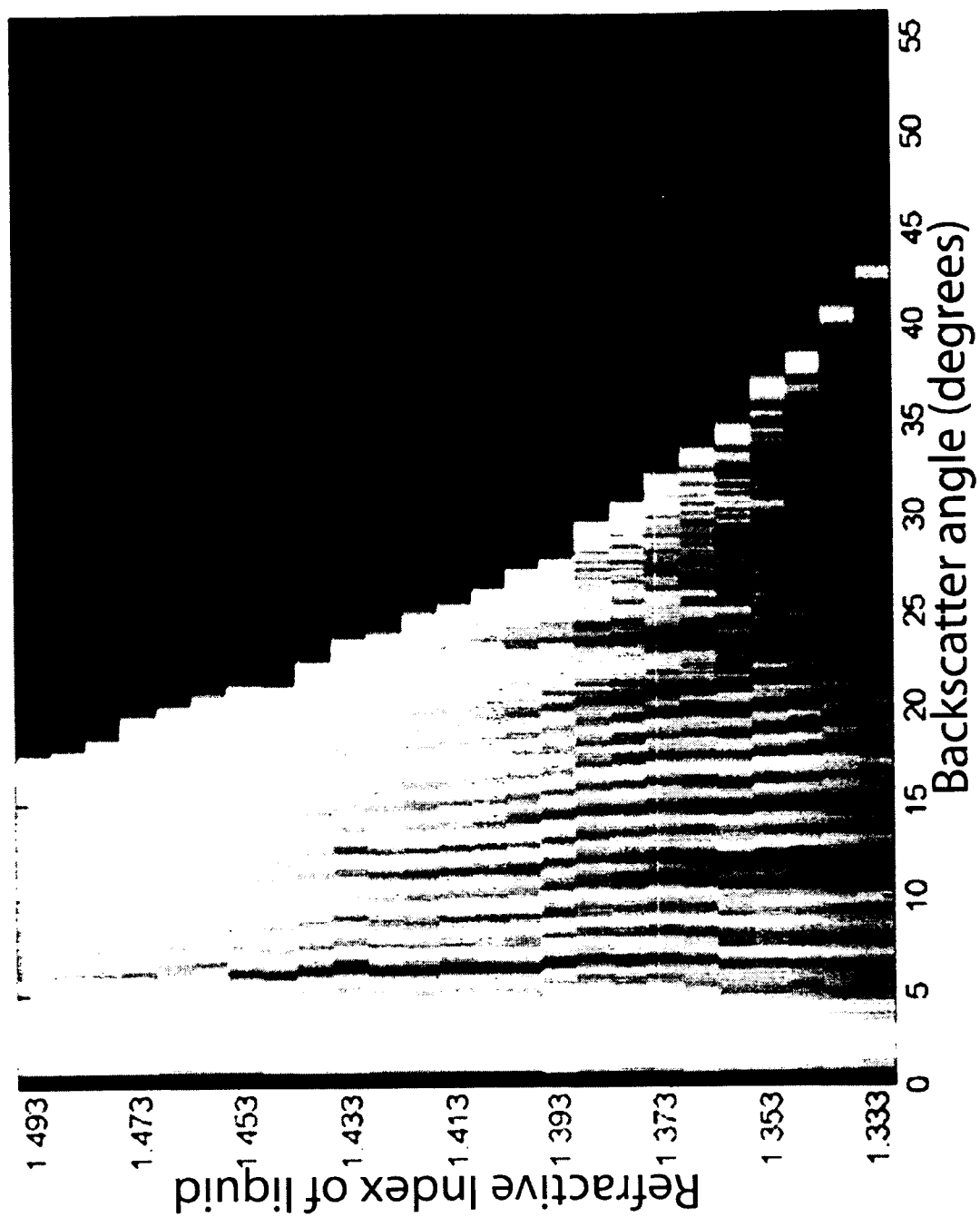
FIG. 10 shows an experimentally obtained pattern for a 542 μm ID/673 μm OD/24 μm coating capillary.
Figure 11:
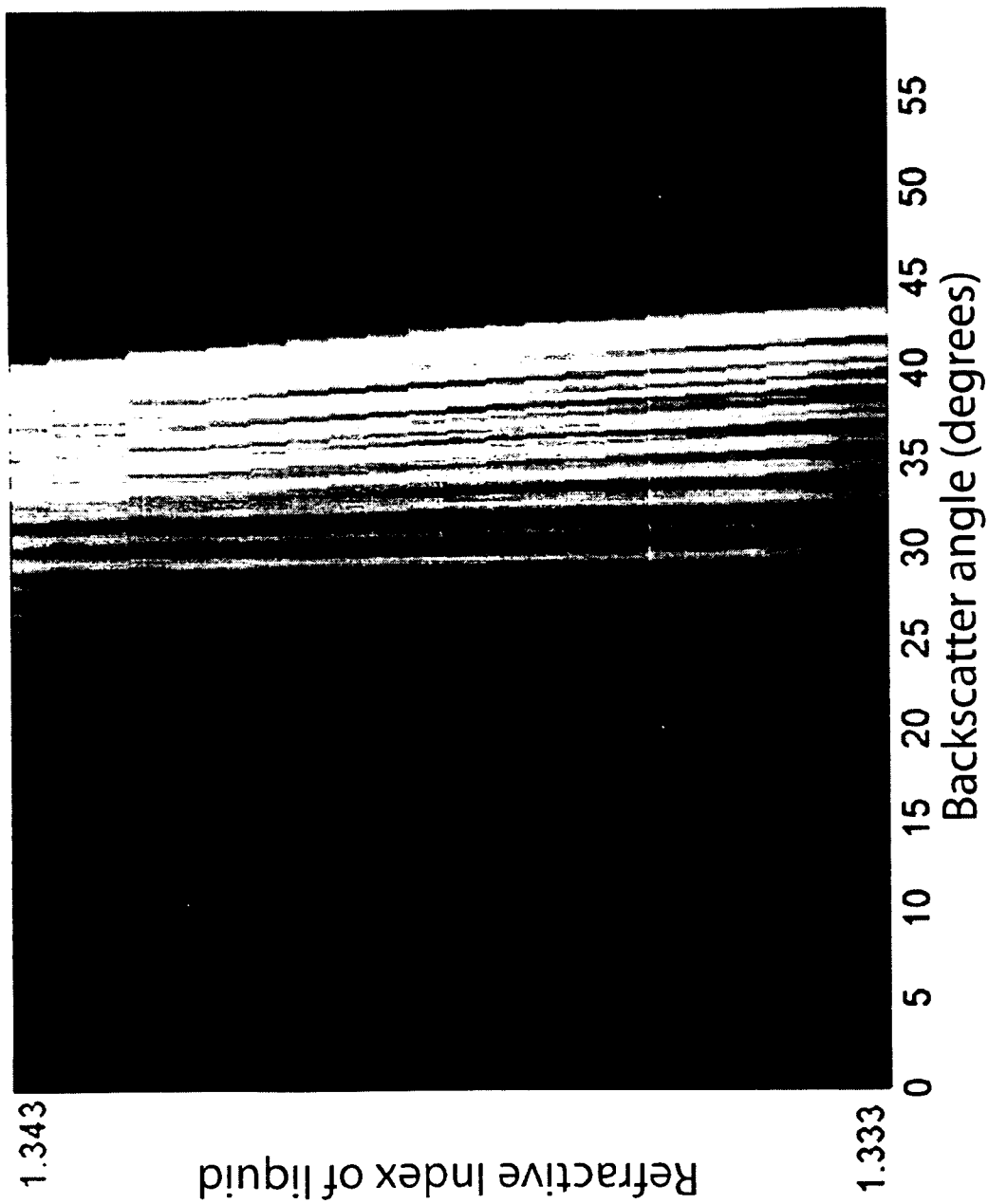
FIG. 11 shows experimentally obtained data from a 542 μm ID/673 μm OD/24 μm coating capillary.

The modeled interference pattern as function of refractive index for a 542 μm ID/673 μm OD/24 um coating capillary is shown in FIG. 9. FIG. 10 shows the experimental results from using a 542 μm ID/673 μm OD/24 um coating capillary. It is seen by comparison to FIG. 9 that the position of the abrupt change in intensity differs from the model, although the behavior is quantitatively the same. Both low and medium frequency variations as well as the abrupt change in intensity level at high reflection angles are seen. The abrupt change in intensity for this capillary occurs in a more relevant interval for dilute aqueous solutions, than it does for the 100 μm ID/165 μm OD/12 μm coating capillary, as indicated by (a).

The experimental and the modeled results show good agreement. The abrupt change in interference pattern is already detectable at the refractive index of water and is experimentally accessible well beyond refractive indices normally considered for aqueous solutions, see point (a) in FIG. 9. The discrepancy between the predicted and the measured angles of the abrupt intensity change may be attributed to material parameter tolerances of the experimental set up as follows: The uncertainty of the dimensions of this capillary is 12 μm and 25 μm for the inner and outer diameter, respectively. This gives an uncertainty of 6.9° in the angle predicted by the model. The uncertainty in refractive index of the polyimide coating (n=1.5–1.8) is causing a further uncertainty in the predicted angle of 3.3°. In FIG. 10, the position of the abrupt change in intensity is monitored as function of refractive index of sucrose solutions. The detection limit for refractive index changes achieved by following the position of this change in position is $2.5 \times 10^{-4}$. From the experiments resulting in FIG. 10 the precision is found to be $2.5 \times 10^{-4}$. Hence we are able to perform an absolute refractive index measurement with accuracy on this level on a nanoliter volume. The main limitations for accuracy such as temperature control and detector resolution are the same as conventional MIBD. The theoretical limit using this approach is therefore similar to the limit achievable by conventional MIBD. It is possible to perform a conventional MIBD measurement simultaneously to our newly proposed method.

As can be seen, the present invention following our concept of investigating a larger range of interference fringes offers fundamentally new applications of the micro interferometric back-scatter detection scheme. We have shown two possible ways of making absolute measurements of the refractive index of liquid in nanoliter probe volumes in a simple optical setup. The improved model based on ray tracing has been used to reveal and explain novel features of the interference pattern: An abrupt change in intensity at large reflection angle is clearly present in the modeled system and in the experimental results. It is shown that this approach enables an absolute determination of the refractive index in the range from 1.33 to 1.5 by using capillary tubes of appropriate dimensions. It has been proven that the model based on ray tracing may be used for describing the MIBD phenomenon. The improved ray tracing model is capable of explaining all the significant features of the MIBD pattern except the stationary high frequency fringes. However, these fringes have been shown to originate from reflections from the edges of the capillary and thereby not being relevant for measuring the refractive index of the liquid within. These improvements of the MIBD scheme will contribute significantly to enhance future applicability of the methodology for analysis of minute volumes of aqueous solutions.

In this specification, unless expressly otherwise indicated, the word "or" is used in the sense of an operator that returns a true value when either or both of the stated conditions is met, as opposed to the operator exclusive or' which requires that only one of the conditions is met. The word "comprising" is used in the sense of "including" rather than in to mean "consisting of."

REFERENCES (1) Valcarcel, M.; Cadenas, S. Trends Anal. Chem., 2002, 21, 211–212.
(2) Hanrahan, G.; Ussher, S.; Gledhill, M.; Achterberg, E. P.; Worsfold, P. J. Trends Anal. Chem., 2002, 21, 233–239.
(3) Schult, K.; Katerkamp, A.; Trau, D.; Grawe, F.; Cammann, K.; Meusel, M. Anal. Chem., 1999, 71, 5430–5435.
(4) Valcarcel, M.; Cadenas, S.; Gallego, M. Trends Anal. Chem., 2002, 21, 251–258.
(5) Zolotov, Y. A.; Ivanov, V. M.; Amelin, V. G. Trends Anal. Chem., 2002, 21, 302–319.
(6) Patel, P. D. Trends Anal. Chem., 2002, 21, 96–115.
(7) Wang, J. Trends Anal. Chem., 2002, 21, 226–232.
(8) Francis, P. S.; Lewis, S. W.; Lim, K. F. Trends Anal. Chem., 2002, 21, 389–400.
(9) Zhou, F.; Aronson, J. T.; Ruegnitz, M. W. Anal. Chem., 1997, 69, 728–733.
(10) Rigby, G. P.; Ahmed, S.; Horseman, G.; Vadgama, P. Anal. Chim. Acta, 1999, 385, 23–32.
(11) Aiello, M.; McLaren, R. Anal. Chem., 2001, 73, 1387–1392.
(12) Oleschuk, R. D.; Harrison, D. J. Trends Anal. Chem., 2000, 19, 379–388.
(13) Lagerwerf, F. M.; van Dongen, W. D.; Steenvoorden, R. J. J. M.; Honing, M.; Jonkman, J. H. G. Trends Anal. Chem., 2000, 19, 418–427.
(14) Lurie, I. S.; Anex, D. S.; Fintschenko, Y.; Choi, W.-Y. J. Chromatogr. A, 2001, 924, 421–427.
(15) Senior, K. Molecular Medicine Today, 1999, 5, 326–327.
(16) Hack, N. J.; Billups, B.; Guthrie, P. B.; Rogers, J. H.; Muir, E. M.; Parks, T. N.; Kater, S. B. J. Neuroscience Methods, 2000, 95, 177–184.
(17) Xia, Y.; Whitesides, G. M. Angew. Chem., 1998, 37, 550–575.
(18) Kutter, J. P. Trends Anal. Chem., 2000, 19, 352–363.
(19) McDonald, J. C.; Duffy, D. C.; Anderson, J. R.; Chiu, D. T.; Wu, H.; Schueller, O. J. A.; Whitesides, G. M. Electrophoresis, 2000, 21, 27–40.
(20) Terry, S. C.; Jerma, J. H.; Angell, J. B. IEEE Transactions on Electron Devices, 1979, 26, 1880–1886.
(21) Heideman, R. G.; Lambeck, P. V. Sensors and Actuators B, 1999, 61, 100–127.
(22) Bornhop, D. J. Appl. Opt., 1995, 34, 3234–3239.
(23) Bornhop, D. J. U.S. Pat. No. 5,325,170, 1994.
(24) Swinney, K.; Markov, D.; Bornhop, D. J. Review of Scientific instruments, 2000, 71, 2684–2692.
(25) Swinney, K.; Markov, D.; Hankins, J.; Bornhop, D. J. Anal. Chim. Acta, 1999, 400, 265–280.
(26) Markov, D.; Bornhop, D. J. Fresenius' Journal of Anal. Chem., 2001, 371, 234–237.
(27) Swinney K.; Bornhop, D. J. Electrophoresis, 2001, 22, 2032–2036.
(28) Kerker, M.; Matijevic, E. J. Opt. Soc. Am., 1961, 51, 506–508.
(29) Watkins, L. S. J. Opt. Soc. Am., 1974, 64, 767–772.
(30) Marcuse. D.; Presby, H. M. J. Opt. Soc. Am., 1975, 65, 367–375.
(31) Horton. R.; Williamson, W. J. J. Opt. Soc. Am., 1973, 63, 1204–1210.
(32) Tarigan, H. J.; Neill, P. Kenmore, C. K.; Bornhop, D. J. Anal. Chem., 1996, 68, 1762–1770.

(33) Pedrotti, F. L.; Pedrotti, L. S. Introduction to optics, 2nd ed.; Prentice-Hall New Jersey, 1996; Chapter 27.
(34) Markov, D.; Swinney, K.; Norville, K.; Lu, D.; Bornhop, D. J. Electrophoresis, 2002, 23, 809–812.

What is claimed is:

1. A method for performing a measurement of refractive index comprising directing a coherent light beam along a light path to impinge on a first light transmissive material and pass there through, to pass through a sample which is to be the subject of the measurement, and to impinge on a further light transmissive material, the sample being located between the first and further materials, detecting reflected light over a range of angles with respect to the light path, the reflected light including reflections from interfaces between different substances including interfaces between the first material and the sample and between the sample and the further material which interfere to produce an interference pattern comprising alternating lighter and darker fringes spatially separated according to their angular position with respect to the light path, and conducting an analysis of the interference pattern to determine there from the refractive index, wherein the analysis comprises observation of a parameter of the interference pattern which is quantitatively related to sample refractive index dependent variations in the intensity of reflections of light which has passed through the sample.

2. A method as claimed in claim 1, wherein said analysis comprises one or both of: (a) the observation of the angle with respect to the light path at which there is an abrupt change in the intensity of the lighter fringes, or (b) the observation of the amplitude of a low frequency component of the variation of intensity between the lighter and darker fringes.

3. A method according to claim 2, wherein the first material and the further material are composed of the same substance.

4. A method as claimed in claim 3, wherein the sample is contained in a flow channel having a cross-sectional depth of up to 1 mm in the direction of the light path.

5. A method as claimed in claim 4, wherein the sample is contained in a capillary tube.

6. A method as claimed in claim 1, wherein at least one said interface involving said sample at which light is reflected is curved in a plane containing said light path, said curved interface being convex in the direction facing the incoming light if it is the interface between the first material and the sample and being concave in the direction facing the incoming light if it is the interface between the sample and the further material.

7. A method as claimed in claim 1, wherein the sample is a liquid.

8. A method as claimed in claim 1, wherein the first and further materials are solid.

9. A method as claimed in claim 1, wherein said range of angles includes angles up to at least 20 degrees.

10. A method as claimed in claim 9, wherein said range of angles includes angles up to at least 40 degrees.

11. Apparatus for use in performing a measurement of refractive index, which apparatus comprises a source of coherent light, a sample holder for receiving a sample upon which to perform said method positioned in a light path from said light source, said sample holder providing a first interface between the sample holder and a sample receiving space in said sample holder and a second interface between said sample receiving space and said sample holder, said first and second interfaces being spaced along said light path, a detector for detecting light reflected in use from a said sample over a range of angles with respect to the light path, the reflected light including reflections from said first and second interfaces which interfere to produce and interference pattern comprising alternating lighter and darker fringes spatially separated according to their angular position with respect to the light path, and data processing means for receiving measurements of light intensity from said detector and for conducting an analysis thereon, wherein the analysis comprises determining a parameter of said interference pattern produced by said reflected light which parameter is quantitatively related to sample refractive index dependent variations in the intensity of reflections of light which has passed through the sample.

12. Apparatus as claimed in claim 11, wherein said data processing means is adapted to perform an analysis which comprises:
    the determination of the amplitude of a low frequency component of the variation of intensity between the lighter and darker fringes.

13. Apparatus according to claim 11, wherein the sample holder locates the sample between a first material and a further material which first and further materials are composed of the same substance.

14. Apparatus as claimed in claim 13, wherein the sample holder is adapted to hold a sample contained in a capillary dimensioned flow channel.

15. Apparatus as claimed in claim 14 wherein the sample holder is a capillary tube.

16. Apparatus as claimed in claim 11, wherein said sample holder is so constructed that at least one of said first and said second interfaces is curved in a plane containing said light path, said curved interface being convex in the direction facing the incoming light if it is the interface nearer said light source in said light path and being concave in the direction facing the incoming light if it is the interface more distant from the light source in the light path.

17. Apparatus as claimed in claim 11, wherein said range of angles includes angles up to at least 20 degrees.

18. Apparatus as claimed in claim 17, wherein said range of angles includes angles up to at least 40 degrees.

19. Apparatus as claimed in claim 11, wherein said data processing means is adapted to perform an analysis which comprises the determination of the angle with respect to the light path at which there is an abrupt change in the intensity of the lighter fringes.

20. Apparatus as claimed in claim 11, wherein said data processing means is adapted to perform an analysis which comprises the determination of the angle with respect to the light path at which there is an abrupt change in the intensity of the lighter fringes and comprises the determination of the amplitude of a low frequency component of the variation of intensity between the lighter and darker fringes.

21. Apparatus as claimed in claim 11, wherein said data processing means is adapted to perform an analysis which comprises one or both of:
    (a) the determination of the angle with respect to the light path at which there is an abrupt change in the intensity of the lighter fringes, or
    (b) the determination of the amplitude of a low frequency component of the variation of intensity between the lighter and darker fringes,
    and wherein the sample holder locates the sample between a first material defining said first interface with said sample and a further material defining said second interface with said sample, which first and second materials are composed of the same substance.

22. Apparatus for use in performing a measurement of refractive index, which apparatus comprises a source of coherent light, a sample holder for receiving a sample upon which to perform said method positioned in a light path from said light source, a detector for detecting light reflected from said sample over a range of angles with respect to the light path, and data processing means for receiving measurements of light intensity from said detector and for conducting an analysis thereon, wherein the analysis comprised determining a parameter of an interference pattern produced by said reflected light which parameter is quantitatively related to sample refractive index dependent variations in the intensity of reflections of light which has passed through the sample, and further comprising a said sample holder, which sample holder is so constructed that there is a first light reflecting interface between a sample receiving space in said sample holder and a first material and a second light reflecting interface between said sample receiving space and a further material, said first and second interfaces being arranged in that order along the light path starting from said light source, wherein at least one of said first and second interfaces is curved in a plane containing said light path, said curved interface being convex in the direction facing the incoming light if it is the interface between the first material and the sample and being concave in the direction facing the incoming light if it is the interface between the sample and the further material.

23. Apparatus as claimed in claim 22, wherein both the first and second interfaces are curved, the first interface being convex towards the light source and the second interface being concave towards the light source.

24. Apparatus as claimed in claim 22, wherein said first material and said second material are composed of the same substance.

* * * * *